(12) United States Patent
Papp

(10) Patent No.: US 10,099,052 B2
(45) Date of Patent: Oct. 16, 2018

(54) MULTI-CHANNEL PHYSIOTHERAPY DEVICE AND PROCEDURE FOR ITS APPLICATION

(71) Applicant: Janos Papp, Budapest (HU)

(72) Inventor: Janos Papp, Budapest (HU)

(\*) Notice: Subject to any disclaimer, the term of this patent is extended or adjusted under 35 U.S.C. 154(b) by 135 days.

(21) Appl. No.: 15/278,035

(22) Filed: Sep. 28, 2016

(65) Prior Publication Data

US 2017/0087362 A1 Mar. 30, 2017

(30) Foreign Application Priority Data

Sep. 29, 2015 (HU) .................................... 1500436

(51) Int. Cl.
| | | |
|---|---|---|
| *A61N 1/00* | (2006.01) | |
| *A61N 1/36* | (2006.01) | |
| *A61N 1/04* | (2006.01) | |
| *A61N 1/378* | (2006.01) | |
| *A61N 1/372* | (2006.01) | |

(52) U.S. Cl.
CPC ....... *A61N 1/36003* (2013.01); *A61N 1/0452* (2013.01); *A61N 1/36014* (2013.01); *A61N 1/372* (2013.01); *A61N 1/3787* (2013.01)

(58) Field of Classification Search
CPC .......................... A61N 1/36003; A61N 1/0452
USPC ........................................................... 607/48
See application file for complete search history.

(56) References Cited

U.S. PATENT DOCUMENTS

| | | |
|---|---|---|
| 6,895,280 B2 | 5/2005 | Meadows et al. |
| 7,499,746 B2 | 3/2009 | Buhlmann et al. |
| 8,565,888 B2 | 10/2013 | Buhlmann et al. |
| 2011/0054570 A1 | 3/2011 | Lane |
| 2011/0160810 A1 | 6/2011 | Griffith |

FOREIGN PATENT DOCUMENTS

| | | |
|---|---|---|
| FR | 2758268 A1 | 7/1998 |
| JP | H04352970 A | 12/1992 |
| WO | WO03032887 A1 | 4/2003 |

*Primary Examiner* — Nadia A Mahmood
(74) *Attorney, Agent, or Firm* — Gokalp Bayramoglu

(57) ABSTRACT

The invention is a multi-channel physiotherapy device, which is fitted with an electrical source, a power supply unit, a photo-coupler, a microprocessor, and an electrode. It is characterized in that the electrical source is connected to a single power supply unit, the power supply unit is connected to the microprocessor, and the microprocessor is connected to the photo-couplers and, through the photo-couplers and the channels, to the electrodes, the number of which is at least approximately equal to the number of photo-couplers and channels.

19 Claims, 1 Drawing Sheet

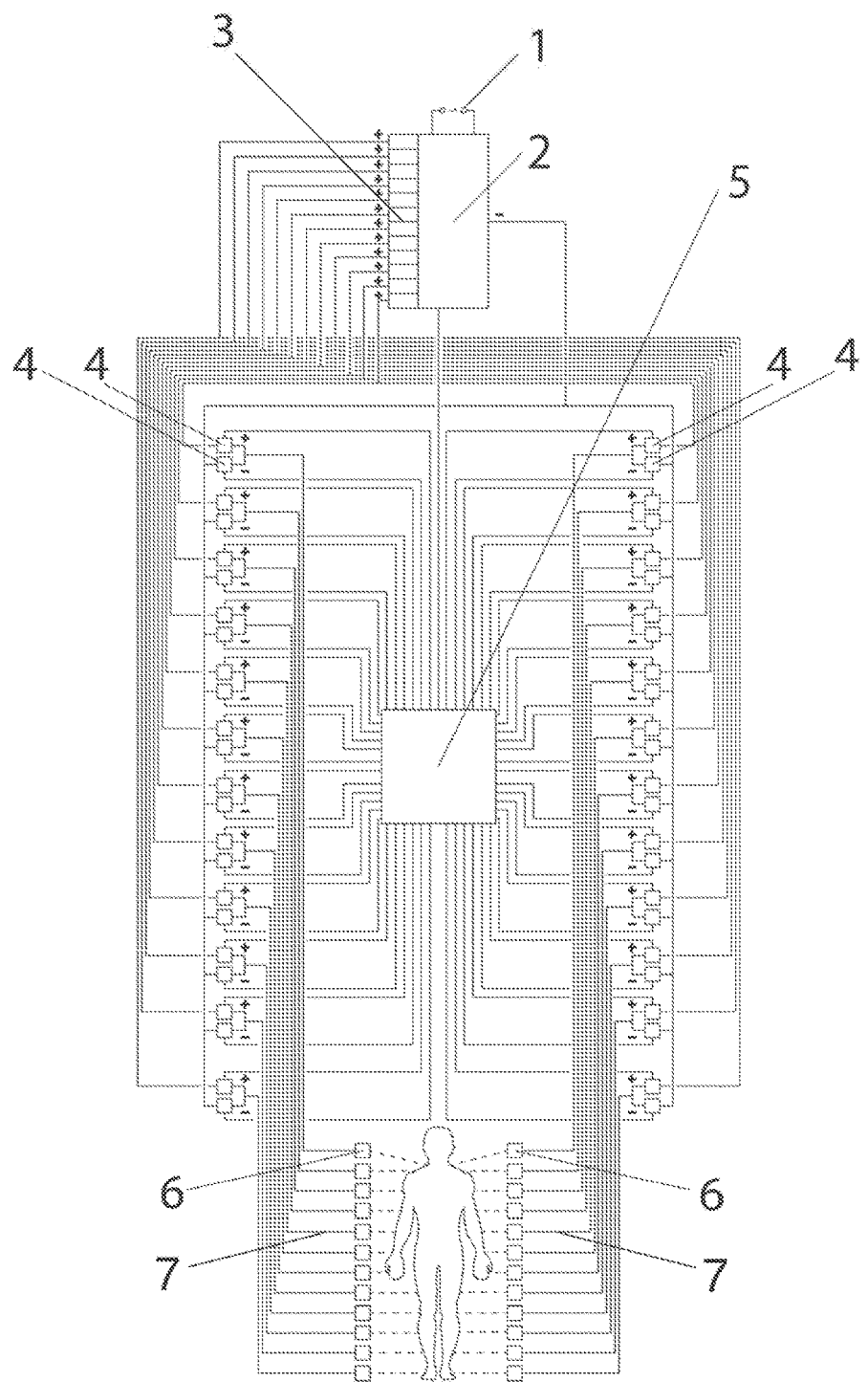

MULTI-CHANNEL PHYSIOTHERAPY DEVICE AND PROCEDURE FOR ITS APPLICATION

TECHNICAL FIELD

The subject of the invention is a multi-channel physiotherapy device, which is fitted with an electrical source, a power supply unit, a photo-coupler, a microprocessor, and an electrode. The subject of the invention also includes the procedure for the application of the device.

BACKGROUND

The following solutions are included in the state of the art.

French patent application No. FR2758268 A1 describes an electric muscle stimulation system, where the electrodes are mounted onto the special suit using Velcro straps, so that they are adjusted to the appropriate muscle groups.

Japanese patent document No. JPH04352970 A describes a unit consisting of 4 electrodes that include wires and carbon fibres, which also includes a foam capable of absorbing water. Its cover is made of flexible silicon.

U.S. Pat. No. 6,895,280 B2 describes a multi-channel muscle stimulation devices fitted with multiple electrodes. U.S. Pat. No. 7,499,746 B2, and its U.S. Pat. No. 8,565,888 B2, also describe an electronic muscle stimulation device. The solution includes at least one electrode and it has multiple channels. The device is also capable of measuring the response from the muscles, the electric impulse. International patent application No. WO03032887 A1 describes a muscle stimulating invention, which measures the impact on the muscles, meaning that it does not provide feedback during use.

Similarly to the above documents, U.S. patent application No. US2011054570 A1 describes a multi-channel electric muscle stimulating device.

U.S. patent application No. US2011160810 A1 also describes a multi-channel electric muscle stimulating device fitted with multiple electrodes.

A disadvantage of the inventions is that they consume a significant amount of energy. For the user, it is also disadvantageous that his body is exposed to a large stimulus at once, and the electric load on the entire body is multiplied. All photo-couplers are fitted with a separate power supply unit, and the entire body is exposed to the total electric performance, meaning that only a portion of it reaches any given muscle.

The purpose of the invention is to eliminate the shortfalls of the known solutions, and to implement an electric stimulating device and a procedure for its application, which operates only with a single power supply unit, consumes less energy, but works with higher efficiency. It is a goal to reduce the electric load the human body is exposed to, while preserving the performance of the stipulating force working on the muscles. It is also a goal to direct the entire electric impulse to a single electrode, meaning that the electric load on the entire body is equal to the performance of a single channel at any given time. Consequently, it is also a goal to achieve separation by channel, meaning that only a single output impulse is active at any time, so that the stimulation of the muscles takes place at different times, while the user has the feeling that he experiences contractions over his entire body simultaneously.

SUMMARY OF THE INVENTION

The inventive step is based on the recognition that an invention that is more advantageous than the earlier ones can be achieved by implementing the device according to claim 1.

In line with the desired purpose, the most general implementation form of the solution according to the invention may be implemented according to claim 1. The most general form of the application procedure is described in the main procedural claim. The various implementation forms are described in the sub-claims.

The solution in general is a multi-channel physiotherapy device, which is fitted with an electrical source, a power supply unit, a photo-coupler, a microprocessor, and an electrode.

A feature of the invention is that the electrical source is connected to a single power supply unit, the power supply unit is connected to the microprocessor, and the microprocessor is connected to the photo-couplers and, through the photo-couplers and the channels, to the electrodes, the number of which is at least approximately equal to the number of photo-couplers and channels.

In another implementation form, the number of channels, photo-couplers, and electrodes each falls between 6 and 14 for each body side.

Another distinctive feature may be that the total output performance of the device is maximum 3.75 Watt.

Another distinctive feature may be that each channel is regulated separately.

In another implementation form, the output performance of one channel is 0.04-0.225 Joule per second.

It is a distinctive feature of the general application of the invention that a single power supply unit is connected to the electrical source, and a microprocessor, photo-couplers, and electrodes, the number of which is at least approximately equal to the number of photo-couplers, are connected to the power supply unit through channels, the number of which is at least approximately equal to the number of photo-couplers and electrodes, and all photo-couplers are served by the single power supply unit.

A distinctive feature of the procedure may be that the output impulses are sent through the channels with a time delay, so that each electrode stimulates the individual muscles at different times.

Another distinctive feature of the procedure may be that a single muscle is stimulated at a given time, so that the muscle stimulation does not exceed 0.225 Joule.

BRIEF DESCRIPTION OF THE DRAWINGS

The invention is described below in more detail on the basis of drawings for the implementation forms.

On the attached drawing, FIG. 1 shows the circuit diagram of the device.

DETAILED DESCRIPTION OF THE EMBODIMENT

FIG. 1 presents the circuit and shows the parts of the device conducting electric muscle stimulation and fitted with multiple channel pairs. The device works with direct current, electricity is provided by the electrical source 1. 9 to 15 V enters power supply unit 2 and is converted to 50 V. It proceeds to photo-couplers 4 through parallel positive poles 3. Quickly connecting photo-couplers 4 provide unidirectional signal and data transmission between the different circuits with different voltage levels. Microprocessor 5 controls opening of the photo-couplers 4 and the amperage coming from power supply unit 2, sets the value for given open channel 7 when photo-coupler 4 belonging to channel 7 is in open position, and microprocessor 5 also stores the pre-written programs. The converted electric current proceeds to electrodes 6, which electrodes 6 are placed onto the appropriate regions and muscles of the human body. The signal set by microprocessor 5 reaches appropriate electrodes 6 through open channels 7, thereby delivering electric stimuli to the given muscles. The device can be used by multiple patients, i.e. users at the same time. The device can have any number of pairs of channels 7. In this implementation form, there are twelve pairs of channels 7. Due to its design, any interference between the individual channel pairs and any crosscurrent in the human body can be excluded. Only a single output impulse is active at any given time, but, due to the quick consecutive channel changes, the delays in the entire routine are undetectable for the human body and it is sensed by the entire body as a one-time flexing of the muscles.

In the course of applying the invention according to the desired result, power is provided for the operation of the device by electrical source 1. Power supply unit 2 converts the current to the desired form, and then it is sent to quickly connecting photo-couplers 4. Photo-couplers 4 correspond to electrodes 6. Signals and data are transferred to given electrode 6 when photo-couplers 4 are in open position Microprocessor 5 controls this process, controls the opening of photo-couplers 4, and sets the appropriate signal. The various muscles of the body are stimulated by electrodes 6 with a slight time delay. Only single channel 7 is active at any given time, but they are changing quickly, so that the body detects only a single flexing of the muscles.

The device described has numerous advantages. One of the advantages is that it allows for this production of quick and delayed square-waves, separated by channels, using a single electrical source. Another new feature and advantage of the solution is that, for each channel pair, the electric impulses discharged onto and reflected by the body can be measured, so various conclusions may be drawn on the basis of the principle of bioresonance. Feedback is an important advantage, it helps the making of measurements, personalized improvements, and progress tracking. The stimulation placed and applied onto the various muscle groups of the body at the same time allows for the improvement of blood circulation and for the improvement of the muscles of patients who may be even laying or even in coma. To this end, only a load of 0.04 Joule needs to be applied onto the body, unlike in the case of other commercially available devices that may have a performance of up to 50 or 60 W. When delivering full output at each channel, a total load of 0.225 Joule is discharged onto the body. This way, the electric load exerted onto the entire body is equal to the performance of a single channel. During average use, the entire body is affected by 0.4 Joule. This significantly reduces power consumption and avoids wastefulness, since there are no power supply units or generators for each channel, and only one power supply unit is used. This also increases efficiency. The essence of the solution is that it reduces the electric load exerted onto the human body, while maintaining the power of electric stimuli on the muscles. Numerous clinical examinations have proven that the developed technology is capable of achieving the same results as traditional devices using voltaic separated channels, and it is in fact even more advantageous from various aspects. The main point of our invention is that it delays in time the impulses discharged through the different channels, meaning that only a single stimulus is applied to the human body at any given time. The greatest advantage of this is that possible cross-impulses between the various channel pairs can be eliminated, and the carefully selected delay frequency makes it possible that the delay in time regarding the muscles remains unnoticeable for the user. Another important advantage is that this design reduces the energy consumption of the device and the output signal performance significantly, and the electric power discharged onto the human body—even taking into account all channels—is equal to the performance of a single channel. This means that the total output performance is maximum 3.75 Watt with total output, which—taking into account the impulse peaks and interim brakes—makes it unique among all the commercially available devices. Another advantage is that a single device can be used to treat multiple patients at the same time. Another important advantage is that the large muscle groups can be stimulated due to the multiple channels that can be used simultaneously while being regulated separately, thereby increasing the circulation and metabolism. This solution may bring about significant improvements in the condition of inactive patients.

In addition to the above examples, the invention may be implemented in other forms and with other manufacturing procedures within the scope of protection.

The invention claimed is:

1. A multi-channel physiotherapy device, comprising: an electrical source, a power supply unit, at least one photo-coupler, a microprocessor, and at least one electrode;
   wherein the electrical source is connected to the power supply unit;
   the power supply unit is connected to the microprocessor;
   the microprocessor is connected to the at least one photo-coupler;
   the microprocessor is connected to each electrode through one of the at least one photo-coupler and a channel;
   a number of electrodes are at least equal to a number of photo-couplers; and
   the number of electrodes are at least equal to a number of channels.

2. The multi-channel physiotherapy device according to claim 1, wherein the number of channels are between 6 and 14, the number of photo-couplers are between 6 and 14, and the number of electrodes are between 6 and 14.

3. The multi-channel physiotherapy device according to claim 1, wherein the total output performance of the device is maximum 3.75 Watt.

4. The multi-channel physiotherapy device according to claim 2, wherein the total output performance of the device is maximum 3.75 Watt.

5. The multi-channel physiotherapy device according to claim 1, wherein each channel is regulated separately.

6. The multi-channel physiotherapy device according to claim 2, wherein each channel is regulated separately.

7. The multi-channel physiotherapy device according to claim 3, wherein each channel is regulated separately.

8. The multi-channel physiotherapy device according to claim 4, wherein each channel is regulated separately.

9. The multi-channel physiotherapy device according to claim 1, wherein the output performance of one channel is 0.04-0.225 Joule per second.

10. The multi-channel physiotherapy device according to claim 2, wherein the output performance of one channel is 0.04-0.225 Joule per second.

11. The multi-channel physiotherapy device according to claim 3, wherein the output performance of one channel is 0.04-0.225 Joule per second.

12. The multi-channel physiotherapy device according to claim 4, wherein the output performance of one channel is 0.04-0.225 Joule per second.

13. The multi-channel physiotherapy device according to claim 5, wherein the output performance of one channel is 0.04-0.225 Joule per second.

14. The multi-channel physiotherapy device according to claim 6 wherein the output performance of one channel is 0.04-0.225 Joule per second.

15. The multi-channel physiotherapy device according to claim 7, wherein the output performance of one channel is 0.04-0.225 Joule per second.

16. The multi-channel physiotherapy device according to claim 8, wherein the output performance of one channel is 0.04-0.225 Joule per second.

17. The multi-channel physiotherapy device of claim 1, wherein output impulses are sent through the channels with a time delay, so that each electrode stimulates individual muscles at different times.

18. The multi-channel physiotherapy device of claim 1, wherein a single muscle is stimulated at a given time, so that the muscle stimulation does not exceed 0.225 Joule.

19. The multi-channel physiotherapy device of claim 17, wherein a single muscle is stimulated at a given time, so that the muscle stimulation does not exceed 0.225 Joule.

\* \* \* \* \*